United States Patent [19]

Geprägs

[11] Patent Number: 4,781,701
[45] Date of Patent: Nov. 1, 1988

[54] SYRINGE FOR MEDICAL PURPOSES

[75] Inventor: Peter Geprägs, Weingarten, Fed. Rep. of Germany

[73] Assignee: Arzneimittel GmbH Apotheker Vetter & Co. Ravensburg, Ravensburg, Fed. Rep. of Germany

[21] Appl. No.: 71,344
[22] PCT Filed: Jul. 11, 1986
[86] PCT No.: PCT/DE86/00285
  § 371 Date: Jun. 16, 1987
  § 102(e) Date: Jun. 16, 1987
[87] PCT Pub. No.: WO88/00479
  PCT Pub. Date: Jan. 28, 1988
[51] Int. Cl.$^4$ .............................................. A61M 5/325
[52] U.S. Cl. ................................................... 604/240
[58] Field of Search ............... 604/240, 241, 242, 243

[56] References Cited

U.S. PATENT DOCUMENTS

| | | |
|---|---|---|
| 2,711,171 | 6/1955 | Dunnican . |
| 2,755,801 | 7/1956 | Morando ............................ 604/242 |
| 2,855,927 | 10/1958 | Henderson . |
| 3,035,616 | 5/1962 | Hamilton . |
| 3,096,763 | 7/1959 | McConnaughey et al. ........ 604/240 |
| 3,115,875 | 12/1963 | Wilburn . |
| 3,372,697 | 3/1968 | Keller . |
| 3,459,177 | 8/1969 | Deuschle . |
| 3,472,227 | 10/1969 | Burke . |
| 3,557,787 | 1/1971 | Cohen . |
| 3,667,652 | 6/1972 | Morane et al. . |
| 3,752,510 | 8/1973 | Windischman et al. . |
| 3,756,235 | 9/1973 | Burke et al. . |
| 3,874,383 | 4/1975 | Glowacki . |
| 3,881,484 | 5/1975 | Gidcumb, Jr. . |
| 4,188,949 | 2/1980 | Antoshkiw . |
| 4,235,235 | 11/1980 | Bekkering . |
| 4,394,863 | 7/1983 | Bartner . |
| 4,405,317 | 9/1983 | Case . |
| 4,439,184 | 3/1984 | Wheeler . |
| 4,464,174 | 8/1984 | Ennis . |
| 4,573,972 | 3/1986 | Kamstra . |
| 4,597,758 | 7/1986 | Aalto et al. . |
| 4,599,082 | 7/1986 | Grimard . |
| 4,668,223 | 5/1987 | Grotenhuis . |

FOREIGN PATENT DOCUMENTS

| | | |
|---|---|---|
| 0144483 | 1/1984 | European Pat. Off. . |
| 0191122 | 2/1985 | European Pat. Off. . |
| 1049059 | 1/1959 | Fed. Rep. of Germany ...... 604/240 |

Primary Examiner—John D. Yasko
Attorney, Agent, or Firm—Herbert Dubno

[57] ABSTRACT

The syringe has a needle-attachment piece which forms a connection neck for affixing the syringe needle and which is held at the cylinder nozzle of the syringe cylinder by a connection piece notched in at the cylinder nozzle. The connection piece is provided with a collar which externally surrounds the connection neck sealing it tightly and mechanically stiffening the same, so that the syringe needle can be held in a stable manner, even when the needle-attachment piece is made of a soft elastic material, in order to provide a perfect seal.

2 Claims, 2 Drawing Sheets

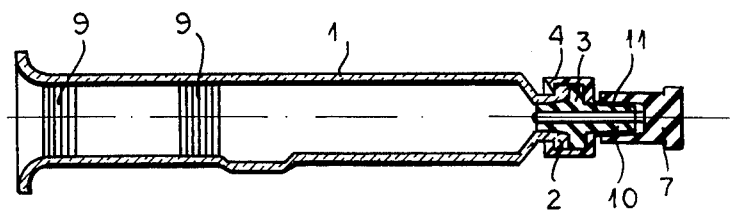
FIG.1
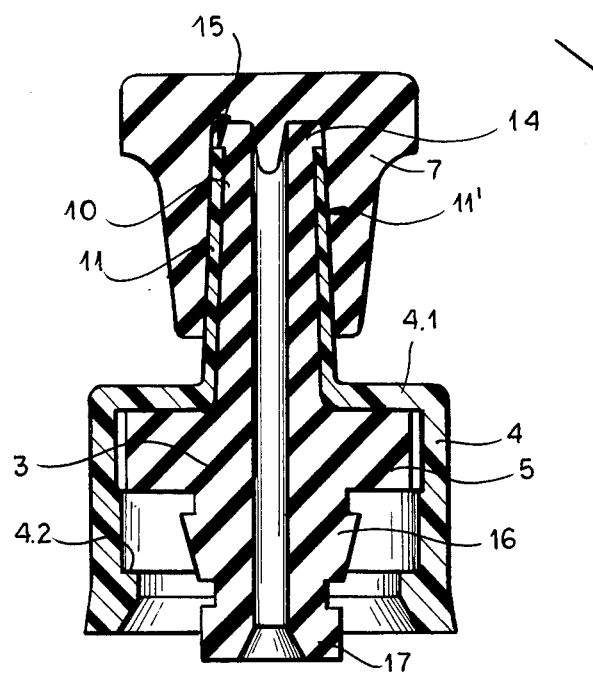
FIG.2
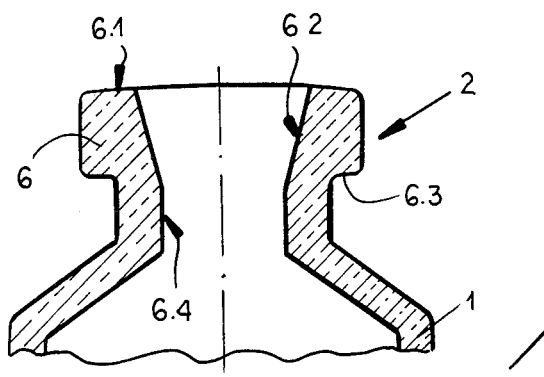

SYRINGE FOR MEDICAL PURPOSES

CROSS REFERENCE TO RELATED APPLICATIONS

This application is a national phase application corresponding to No. PCT/DE86/00285 filed July 11, 1987.

FIELD OF THE INVENTION

The invention relates to a syringe for medical purposes, with a needle attachment fitted on the cylindrical outlet of the syringe body forming a connection neck for attaching the syringe needle, the attachment having a connection piece, notched in at the cylinder nozzle and connecting the needle attachment to the syringe cylinder, whereby the needle attachment is made of an elastic rubber material and the connection piece is made of a synthetic material considerably more rigid than the rubber material.

BACKGROUND OF THE INVENTION

Syringes of this type are described in the not published European patent application No. 84 100 711.5 and have the advantage that the needle attachement and the connection piece can be mounted easily even when the syringe is already filled and can afford a safe sealing of the syringe cylinder. For assembly it is sufficient to fit the coupling piece over the attachment placed on the cylinder nozzle and to push until it is securely lodged at the cylindrical nozzle. The syringe needle can be vulcanized in the connection neck protruding from the coupling piece or it can be glued therein with a heat-resistant glue. It also can be omitted at first, and just before the syringe is used, can be inserted in or fitted on the connection neck, for which purpose a luer cone can be provided onto which a needle guide sleeve carrying the needle can be fitted.

Generally, the luer cone can be recommended also in the case of differently attached needles because it makes it possible to fit over the syringe needle a cap receiving and protecting the same. If the syringe needle is attached on the connection neck only immediately before the use of the syringe, the exit of the needle attachment channel for the passage of the injectable substance can be closed by a so-called tip-cap, fitted on the luer cone and having a central projection reaching into the channel and sealing same.

In such syringes, the problem arises that in order to provide a good and reliable seal at the cylinder nozzle, the needle attachment is usually made of soft elastic material, which leads, on the other hand, to insufficient stiffness in the area of the connection neck to safeguard the mechanical stability of the needle.

OBJECT OF THE INVENTION

It is the object of the invention to provide an improved syringe of the afore-described kind, so that even when the needle attachment is sufficiently soft and elastic to provide a seal for the cylinder nozzle, the syringe is still held with sufficient mechanical stability at the connection neck.

SUMMARY OF THE INVENTION

This object is attained according to the invention by providing the connection piece with a collar which surrounds the connection neck in a tightly sealing manner and thereby confers mechanical rigidity to the same.

The collar surrounds the connection neck like a jacket and is in itself rigid enough to safely prevent bending deformations of the connection neck, thereby conferring a high mechanical stability to the needle junction at the needle attachment. Due to its soft elastic characteristics, the connection neck provides a secure seal against the collar, so that, in the case of the syringe according to the invention, it is possible not only to vulcanize or glue the syringe needle in the connection neck, but also to affix it externally on the collar with a guide sleeve carrying the needle, whereby again it is recommended to shape the collar with a luer cone on its outer surface. Further, a preferred embodiment of the invention is characterized in that at the needle end the connection neck forms an elastic annular shoulder overlapping outwardly and radially the frontal annular surface of the collar up to the external jacket surface of the collar, forming an annular seal against a guide sleeve carrying the syringe needle, affixed to the collar. In addition, within the framework of the invention, it is possible to close off the collar at the needle end with a frontal wall into which the syringe needle which reaches through the frontal wall into the connection neck, is sealingly inserted. In any case, a cap protecting the syringe needle can be slipped on the outside of the collar or the needle guide sleeve.

BRIEF DESCRIPTION OF THE DRAWING

In the following, the invention is described more fully with the aid of the embodiments represented in the drawing, in:

FIG. 1, is an axial section of a syringe according to the invention with a plunger indicated only schematically;

FIG. 2 is an enlarged detail exploded view of the frontal end of the syringe cylinder and of the needle attachment.

SPECIFIC DESCRIPTION

Figure 3:
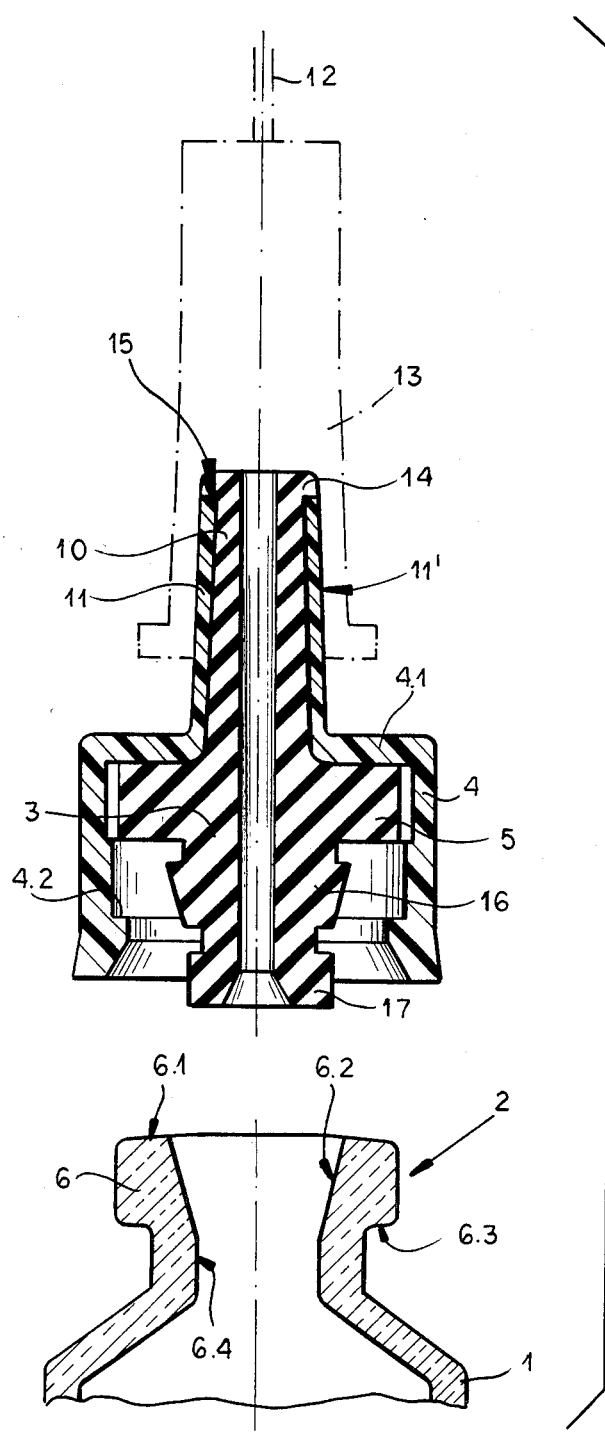
FIG. 3 is a view similar to FIG. 2 of a modified embodiment.

In the drawing, a twin-chamber syringe has two syringe plungers 9 a syringe cylinder or barrel 1 with a 1, its barrel outlet 2. The needle attachment 3 is externally applicable to the barrel outlet in axial direction.

The needle attachment 3 is held by a connection piece 4, for which purpose the barrel outlet 2 and the needle attachment 3 each have an external collar 5, 6 and both external collars 5, 6 are axially pressed against each other by the connection piece 4, which engages over them.

The needle attachment 3 is provided with a connection neck 10 for the connection of the syringe needle. The connection piece 4 forms a collar 11, which externally surrounds the connection neck 10, sealing it tightly and stiffening it, if the needle attachment 3 is made of a soft elastic rubber material in order to provide a secure seal for the cylinder nozzle 2 and the connection piece 4 is made of an elastically considerable more rigid synthetic material, in comparison thereto. As long as no needle is attached to it, the needle attachment piece 3 can be closed by a tip-cap 7, as shown in FIGS. 1 and 2. If a syringe needle is inserted in the needle attachment piece 3, a needle-protection cap, not shown in the drawing, can be slid over the connection neck 10 or the collar 11. Further, for the needle connection there is the possibility shown in FIG. 3 to affix the syringe needle 12 externally, by sliding a needle guide sleeve 13 over the connection neck 10 and the collar 11. In all cases, the collar 11 is thereby shaped as luer cone at its external surface 11 . In FIG. 2, the connection neck 10 has on its needle side an elastic annular shoulder 14 which radially outwardly overlaps the frontal annular surface 15 of the collar 11 up to the external surface 11' of the collar 11, forming an annular seal against the conical inner surface of the needle guide sleeve 13 or of the tip cap 7, slid over the collar 11.

The barrel outlet or tip 2 which is an integral part of the syringe cylinder 1 has an internal surface 6.2 which is frustoconical and extends to the frontal surface 6.1 on the needle side of its outer collar 6 and which widens towards the needle side. The needle attachment piece 3, consisting especially of rubber, has a conical part 16 which rests against the conical inner surface 6.2 of the cylinder nozzle 2, when the needle attachment piece 3 is already mounted. The connection piece 4, which engages over the external collar 5 of the needle attachment piece 3 with an annular flange 4.1, is elastically lodged at the cylinder nozzle 2 with an inner shoulder 4.2 engaging over the frontal face 6.3 facing the cylinder of the external collar 6. In the cylinder nozzle 2, towards the cylinder side, the conical inner surface 6.2 is followed by a cylindrical inner surface 6.4, corresponding to the cylindrical part 17 on the needle attachment 3, which, when the needle attachment piece 3 is mounted at the tip 2 rests with its cylindrical outer surface against the cylindrical inner surface 6.4 of the tip 2.

I claim:

1. A syringe for medical purposes, comprising:

a syringe body adapted to receive a plunger and provided at an outlet end with an outlet tip;

a needle attachment abutting said tip and communicating with said syringe body therethrough, said needle attachment being provided with an elongated connection neck extending away from said tip, said needle attachment and said connection neck being composed of an elastomeric material; and a tubular connection piece surrounding said needle attachment and engaging over said tip to secure said needle attachment to said syringe body, said connection piece having a collar extending along said connection neck toward a free end of said connection neck remote from said tip, said connection piece being composed of a synthetic material more rigid than said elastomeric material, said connection neck being formed at said free end with an annular shoulder abutting an end surface of said collar and extending radially outwardly to an outer surface of said collar to lie flush therewith and form an annular seal for a tip cap or a needle-carrying sleeve adapted to be slid onto said neck and said collar.

2. The syringe defined in claim 1 wherein said collar has a conical taper corresponding to that of a Luer cone.

* * * * *